United States Patent [19]

Nishio et al.

[11] Patent Number: 4,629,793
[45] Date of Patent: Dec. 16, 1986

[54] 2,3-DI-SUBSTITUTED-5,6-DIHYDROIMIDAZO [2,1-B] THIAZOLE, ITS SALTS, PRODUCTION THEREOF AND ANTI-INFLAMMATORY AGENT CONTAINING THE SAME

[75] Inventors: Kazuo Nishio, Saitama; Isao Chiyomaru, Shizuoka; Katsuo Anma, Saitama; Kazuko Yamamoto, Shizuoka; Hiroshi Ohno, Shizuoka; Noriyasu Takayanagi, Shizuoka, all of Japan

[73] Assignees: Toyo Jozo Kabushiki Kaisha, Shizuoka; Kumiai Chemical Industry Co., Ltd., Tokyo, both of Japan

[21] Appl. No.: 741,616

[22] Filed: Jun. 5, 1985

Related U.S. Application Data

[60] Division of Ser. No. 600,011, Apr. 13, 1984, Pat. No. 4,556,669, which is a continuation of Ser. No. 367,600, Apr. 12, 1982, abandoned.

[30] Foreign Application Priority Data

Apr. 10, 1981 [JP] Japan .................................. 56-54166

[51] Int. Cl.$^4$ .......................................... C07D 513/14
[52] U.S. Cl. ..................................................... 548/154
[58] Field of Search ........................................... 548/154

[56] References Cited

U.S. PATENT DOCUMENTS 4,103,016  7/1978  Moser .................................. 424/270

Primary Examiner—Robert Gerstl
Attorney, Agent, or Firm—Young & Thompson

[57] ABSTRACT

Compounds of the formula

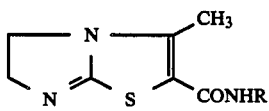

wherein R is

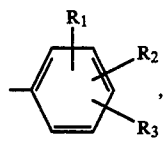

in which $R_1$, $R_2$ and $R_3$ are the same or different and are selected from the group consisting of hydrogen, chlorine, bromine, lower alkyl, lower alkoxy and naphthyl, provided that when $R_1$ is lower alkyl, $R_2$ and $R_3$ are hydrogen, chlorine, bromine or lower alkoxy, or a pharmaceutically acceptable salt thereof, have anti-carrageenin edema activity, and are useful as anti-inflammatory agents and immuno modulators. They are produced by reacting an amide of the formula

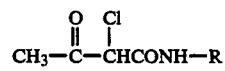

wherein R has the same meanings hereinabove, with N,N'-ethylene thiourea.

15 Claims, No Drawings

2,3-DI-SUBSTITUTED-5,6-DIHYDROIMIDAZO [2,1-B] THIAZOLE, ITS SALTS, PRODUCTION THEREOF AND ANTI-INFLAMMATORY AGENT CONTAINING THE SAME

This application is a division of application Ser. No. 600,011, filed Apr. 13, 1984, now U.S. Pat. No. 4,556,669, which is a file wrapper continuation of Ser. No. 367,600, filed Apr. 12, 1982 and now abandoned.

This invention relates to novel imidazothiazole derivatives, their salts, a method for the production thereof, and anti-inflammatory compositions containing the same. More particularly, this invention relates to 2,3-di-substituted-5,6-dihydroimidazo [2,1-b] thiazole, its salts, a method for the production thereof, and anti-inflammatory compositions containing the same.

Heretofore, levamisol having an imidazothiazole ring of the formula

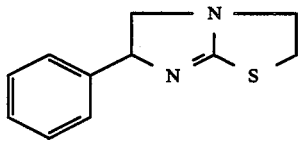

has been known as an antirheumatoidal agent or antitumor agent. Furthermore, an imidazo [2,1-b] thiazole derivative of the formula

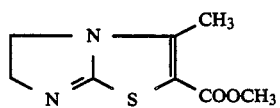

[Tetrahedron, 31 (7), 725–731 (1975)] and imidazo [2,1-b] thiazole derivatives of the formula

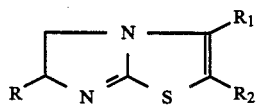

wherein R is hydrogen or methyl, $R_1$ is methyl, phenyl, phenyl substituted with chlorine, bromine or nitro, and $R_2$ is hydrogen or phenyl, [Australian J. Chem., 26 (2), 435–456 (1973)], have been known as agents having the same pharmacological activity of levamisol.

Anti-inflammatory-active 5,6-dihydro-imidazo [2,1-b] thiazole derivatives of the formula

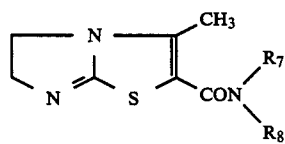

wherein $R_7$ and $R_8$ are each independently hydrogen, monofluorophenyl, trifluorophenyl or trimethylphenyl, have also been reported. [Japan. Pat. Unexamined Publ., No. 52-106893, U.S. Pat. No. 4,224,334]. However, an effective dose of these derivatives per oral administration for carrageenin edema is 200 mg/kg and shows extremely weak anti-inflammatory activity.

We have found that imidazo [2,1-b] thiazole derivatives having specific substituents have lower toxicity as compared with levamisol, have anti-carrageenin edema activity, and are useful an anti-inflammatory agents and immuno modulators.

An object of the present invention is to provide 2,3-di-substituted-5,6-dihydro-imidazo [2,1-b] thiazoles of the formula

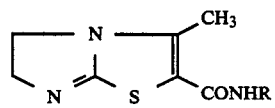

wherein R is

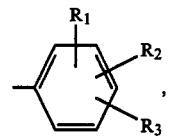

in which $R_1$, $R_2$ and $R_3$ are the same or different and are selected from the group consisting of hydrogen, chlorine, bromine, lower alkyl, lower alkoxy and naphthyl, provided that when $R_1$ is lower alkyl, $R_2$ and $R_3$ are hydrogen, chlorine, bromine or lower alkoxy, or a pharmaceutically acceptable salt thereof.

Another object of the present invention is to provide anti-inflammatory compositions comprising one of the above 2,3-di-substituted-5,6-dihydroimidazo [2,1-b] thiazoles or its pharmaceutically acceptable salts, in admixture with a pharmaceutically acceptable excipient.

A further object of the present invention is to provide a process for the production of these novel imidazo [2,1-b] thiazole derivatives.

Examples of the pharmaceutically acceptable salts are the hydrochloride, sulfate, carbonate, nitrate, bromide, phosphate, sulfonate, acetate, oxalate, tartrate, citrate, malate, glutamate, aspartate or other known organic acid salts.

Examples of the novel imidazo [2,1-b] thiazole derivatives and salts thereof are shown in Table 1.

TABLE 1

| Compound No. | R | m.p. (°C.) | properties |
|---|---|---|---|
| 1 | —C₆H₅ | 204~205 | white powdery crystals |
| 2 | —C₆H₅·HCl | 252~256 | white powdery crystals |
| 3 | 2-Cl-C₆H₄ | 212~213 | white powdery crystals |
| 4 | 2-Cl-C₆H₄·HCl | 261~264 | white powdery crystals |

TABLE 1-continued

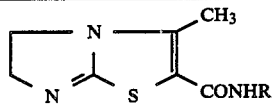

| Compound No. | R | m.p. (°C.) | properties |
|---|---|---|---|
| 5 | —C₆H₄—Cl (4-Cl) | 261~263 | white powdery crystals |
| 6 | —C₆H₄—Cl·HCl | 273~275 | white powdery crystals |
| 7 | 2,4-diCl-C₆H₃— | 217~219 | white powdery crystals |
| 8 | 2,4-diCl-C₆H₃—·HCl | 252~254 | white powdery crystals |
| 9 | —C₆H₄—CH₃ | >250 | white prismatic crystals |
| 10 | 3-Cl-4-CH₃-C₆H₃—·HCl | >250 | white prismatic crystals |
| 11 | 2-C₂H₅-C₆H₄—·HCl | 239~249 | white prismatic crystals |
| 12 | 2-Cl-C₆H₄—·HCl | >250 | white prismatic crystals |
| 13 | 3-CH₃-4-Cl-C₆H₃—·HCl | >250 | white prismatic crystals |
| 14 | —C₆H₄—OC₂H₅·HCl | 246~250 | white prismatic crystals |
| 15 | 2-Cl-3-Cl-C₆H₃—·HCl | >250 | white prismatic crystals |
| 16 | —C₆H₄—Br·HCl | >250 | white scaly crystals |
| 17 | 2,3-diCl-C₆H₃—·HCl | >250 | white prismatic crystals |
| 18 | 3,5-diCl-C₆H₃—·HCl | >250 | pale yellowish prismatic crystals |

TABLE 1-continued

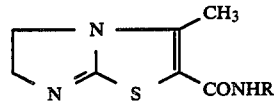

| Compound No. | R | m.p. (°C.) | properties |
|---|---|---|---|
| 19 | 2,4,5-triCl-C₆H₂—·HCl | >250 | pale yellowish prismatic crystals |
| 20 | 2,4,6-triCl-C₆H₂—·HCl | >250 | white powdery crystals |
| 21 | 2-CH₃O-4-Cl-5-OCH₃-C₆H₂—·HCl | 254~256 | white powdery crystals |
| 22 | 2-CH₃O-4-Cl-C₆H₃—·HCl | >250 | white powdery crystals |
| 23 | naphthyl·HCl | >250 | white powdery crystals |
| 24 | —C₆H₄—CH₃ | >250 | white powdery crystals |
| 25 | 2-Cl-4-CH₃-C₆H₃— | 240~242 | white powdery crystals |
| 26 | 2-C₂H₅-C₆H₄— | 178~180 | white prismatic crystals |
| 27 | 2-Cl-C₆H₄— | 184~187 | white powdery crystals |
| 28 | 2-CH₃-4-Cl-C₆H₃— | 234~235 | pale yellowish powdery crystals |
| 29 | —C₆H₄—OC₂H₅ | 220~225 | white powdery crystals |
| 30 | 2,4-diCl-C₆H₃— | >250 | pale yellowish powdery crystals |
| 31 | —C₆H₄—Br | 250 | white powdery crystals |

TABLE 1-continued

| Compound No. | R | m.p. (°C.) | properties |
|---|---|---|---|
| 32 |  | 230 | pale yellowish powdery crystals |
| 33 |  | >250 | white powdery crystals |
| 34 |  | 249~251 | white powdery crystals |
| 35 | 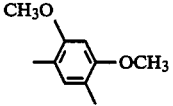 | 218~220 | white powdery crystals |
| 36 | 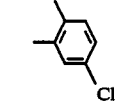 | 254~256 | white powdery crystals |
| 37 |  | >250 | white powdery crystals |
| 38 | 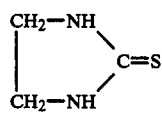 | 122~129 | white powdery crystals |

A process for production of a 2,3-di-substituted-5,6-dihydroimidazo [2,1-b] thiazole or a pharmaceutically acceptable salt thereof, according to the present invention, is that an amide of the formula

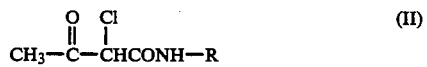 (II)

wherein R has the same meanings hereinabove, is reacted in equimolar ratio with N,N'-ethylene thiourea of the formula $$\begin{array}{c} CH_2-NH \\ | \quad\quad\quad\quad C=S \\ CH_2-NH \end{array}$$

to obtain a compound of the formula

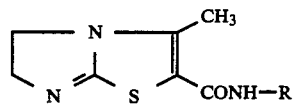

wherein R has the same meanings hereinabove.

The reaction schema of the above reaction is illustrated as follows:

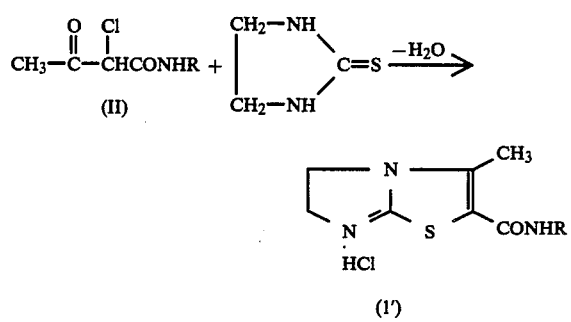

Examples of the solvent used in the above reaction are benzene, toluene, xylene, acetone, methyl ethyl ketone, dimethylformamide, dimethylacetamide, dimethylsulfoxide, acetonitrile, ether, tetrahydrofuran, dioxane or water.

The reaction temperature range is $-5°$ C. to $100°$ C., preferably $20°$ to $80°$ C. Reaction time is 1 to 6 hours, and the present compound can be obtained with higher yield and purity under these conditions.

The free base of compound [I] can be prepared by treating the hydrochloride of compound [I] with a base, for example, an inorganic base such as sodium hydroxide, potassium hydroxide, potassium carbonate, sodium carbonate or sodium bicarbonate, or an organic base such as pyridine or triethylamine. Other salts of compound [I] can be prepared by treating the above hydrochloride or free base with the corresponding acid such as sulfuric acid, carbonic acid, nitric acid, hydrobromic acid, phosphoric acid, sulfonic acid, acetic acid, oxalic acid, tartaric acid, citric acid, malic acid, glutamic acid or aspartic acid.

The starting material for the process fo the present invention, of the formula

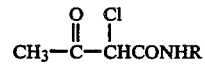

can be prepared by the following reaction schema. [Chem. Abstracts, 19, 43 (1935), ibid., 74, 42102t (1970)].

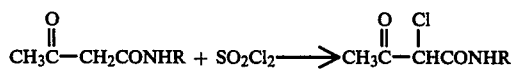

The pharmacological properties of the compound [I] are illustrated as follows:

ANTI-CARRAGEENIN EDEMA ACTION (Experimental method)

Fasting Wister rats, male, 5–6 weeks in age, five in one group, were injected subcutaneously in the sole of the caudal foot with 1% lambda carrageenin (0.05 ml), and the increase in the volume of the foot was measured at alliquot times. Then the compound of the invention was suspended in 0.3% CMC and administered orally one hour before carrageenin injection. 0.3% CMC alone was administered as a control. The minimum effective dose was determined by the minimum dosage amount which shows significant inhibition of edema 3 hours after carrageenin injection.

| Compound No. | Minimum effective dose mg/kg, p.o. | Compound No. | Minimum effective dose mg/kg, p.o. |
| --- | --- | --- | --- |
| 1 | 100 | 14 | 50 |
| 2 | 50 | 15 | <25 |
| 4 | <25 | 16 | 50 |
| 5 | 50 | 19 | 100 |
| 6 | <25 | 21 | 100 |
| 7 | 100 | 22 | 100 |
| 10 | 50 | 30 | <25 |
| 11 | 50 | 32 | 50 |
| 13 | 50 | | |

Compound [I] of the present invention shows 10–40 times lower acute toxicity in mice, when administered orally, then levamisol, and strong anti-carrageenin edema activity. Compound [I] also has strong suppressive action on chronic inflammation such as adjuvant arthritis in rats, by per oral administration, and strong analgesic action, assayed by the acetic acid stretching method, in mice by per oral administration; however, it has extremely weak lesionic activity on gastric mucosa. In general, immuno-suppressors such as levamisol, basis non-steroidal anti-inflammatory agents, steroidal anti-inflammatory agents, azathioprine and cyclophosphamide, and specific anti-rheumatoid agents such as D-penicillamine and gold sodium thiomalate, do not inhibit the heat denaturation of bovine serum albumin but rather stimulate the protein heat denaturation. However, compound [I] of the present invention, having a basic nature, like the acidic non-steroidal anti-inflammatory agents, suppresses the heat denaturation of bovine serum albumin.

Also, compound [I] has suppressive activity against delayed-type foot pad reactions relating to cellular immune mechanisms in mice, immuno modulator activity and antitumor activity.

Compound [I], in the form of an anti-inflammatory composition, can be administered orally in the form of tablets, powder, capsules or granules, which can contain in admixutre conventional vehicles or excipients such as calcium carbonate, calcium phosphate, corn starch, potato starch, sugar, lactose, talc or magnesium stearate. The preparation can be a liquid preparation such as an oily suspension, a solution or a syrup. Parenteral administration can be effected, for example, with an injectable preparation.

The following examples illustrate the present invention:

EXAMPLE 1

2-(3,4-dichlorophenylcarbamoyl)-3-methyl-5,6-dihydroimidazo [2,1-b] thiazole hydrochloride (compound 15):

Compound 15 was synthesized according to the following reaction schema:

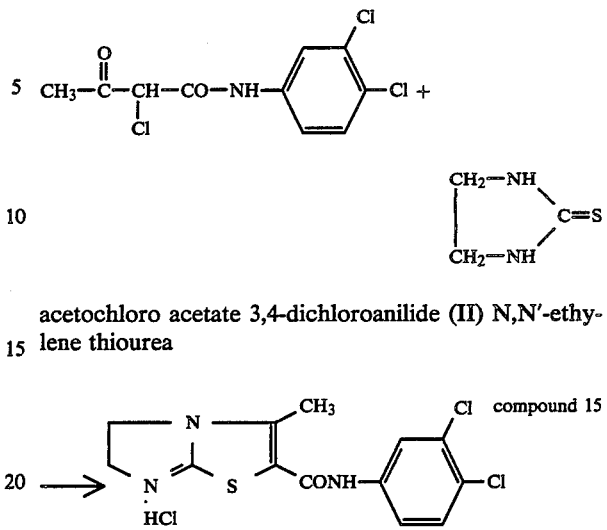

acetochloro acetate 3,4-dichloroanilide (II) N,N'-ethylene thiourea

Compound (II) (14.0 g, 0.05M) and N,N'-ethylene thiourea (5.7 g, 0.056M) dissolved in methyl ethyl ketone (200 ml) were refluxed with stirring for 3 hours. A paste-like substance was formed at first, and then a precipitate was observed. The precipitate was filtered warm. The filtrate was washed with acetone and dried to obtain compound 15 (16.5 g, yield: 90.7%).

m.p.: >250° C., white prisms.

Compound 15 displayed analgesic action (assayed by the acetic acid stretching method) at a dose of 25 mg/kg, administered orally in mice, and inhibited and the adjuvant arthritis of rats at a dose of 1–10 mg/kg, when administered orally. Acute toxicity (mice, p.o.): >4000 mg/kg.

EXAMPLE 2

2-phenylcarbamoyl-3-methyl-5,6-dihydro-imidazo [2,1-b] thiazole hydrochloride (compound 2):

Acetochloroacetate anilide (10.5 g, 0.05M) and N,N'-ethylene thiourea (6.0 g, 0.06M) dissolved in acetone (180 ml) were refluxed for 6 hours with vigorous stirring. A gummy substance was formed during the reaction and after a few minutes a white precipitate was formed. The reaction mixture was cooled and the precipitate was filtered at 30° C. to obtain compound 2 as white powdery crystals. (12.3 g, yield: 83.1%).

m.p.: 252°–256° C.

EXAMPLE 3.

2-(2-chlorophenylcarbamoyl)-3-methyl-5,6-dihydroimidazo [2,1-b] thiazole hydrochloride (compound 4):

Acetochloroacetate 2-chloro anilide (12.3 g, 0.05M) and N,N'-ethylene thiourea (6.2 g, 0.062M) were refluxed in benzene (250 ml) for 4 hours. The precipitate was filtered hot to obtain compound 4 as white powdery crystals. (14.1 g, yield: 85.4%).

m.p.: 261°–264° C.

EXAMPLE 4

Compounds 6 and 8–23 were synthesized according to the following reaction schema by the process in Example 1:

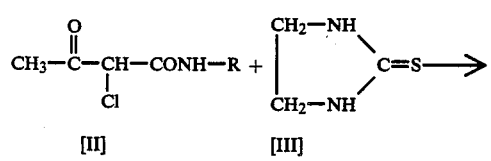

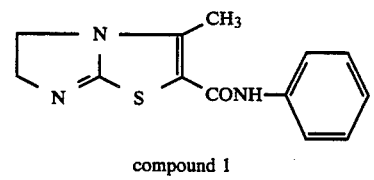

compound 1

| Compound No. | Reaction reagent [II] R | amount used g (0.05 M) | Reaction reagent [III] amount used | | Reaction conditions | | | Compound [I] yield | |
|---|---|---|---|---|---|---|---|---|---|
| | | | g | (M) | solvent (ml) | temperature °C. | time hr. | g | (%) |
| 6 | —C$_6$H$_4$—Cl(4) | 12.3 | 6.2 | (0.062) | DMF (150) | 75–80 | 2 | 13.2 g | (80.4%) |
| 8 | —C$_6$H$_3$—Cl$_2$(2,5) | 14.1 | 6.6 | (0.065) | MEK (200) | 80 | 3 | 13.5 g | (74.3%) |
| 9 | —C$_6$H$_4$—CH$_3$(4) | 11.3 | 6.0 | (0.060) | Dioxane (150) | 75 | 4 | 14.1 g | (91.0%) |
| 10 | —C$_6$H$_3$(Cl(2), CH$_3$(4)) | 13.0 | 5.9 | (0.058) | Acetone (250) | 60 | 6 | 15.5 g | (90.0%) |
| 11 | —C$_6$H$_4$—C$_2$H$_5$(2) | 12.0 | 5.6 | (0.055) | Xylene (250) | 80 | 5 | 15.1 g | (93.4%) |
| 12 | —C$_6$H$_4$—Cl(3) | 12.3 | 6.2 | (0.062) | MEK (200) | 80 | 4 | 14.0 g | (84.8%) |
| 13 | —C$_6$H$_3$(CH$_3$(2), Cl(4)) | 13.0 | 6.0 | (0.060) | DMAC (150) | 80 | 2 | 15.0 g | (87.1%) |
| 14 | —C$_6$H$_4$—OC$_2$H$_5$(4) | 13.6 | 5.3 | (0.052) | Toluene (250) | 85 | 5 | 13.3 g | (78.3%) |
| 16 | —C$_6$H$_4$—Br(4) | 14.5 | 6.0 | (0.060) | DMSO (150) | 80 | 3 | 15.3 g | (82.0%) |
| 17 | —C$_6$H$_3$—Cl$_2$(2,4) | 14.1 | 6.3 | (0.062) | DMSO (150) | 80 | 6 | 15.7 g | (86.3%) |
| 18 | —C$_6$H$_3$—Cl$_2$(3,5) | 14.1 | 6.4 | (0.063) | DMF (150) | 80 | 3 | 13.6 g | (84.1%) |
| 19 | —C$_6$H$_2$—Cl$_3$(2,4,6) | 15.9 | 7.1 | (0.070) | MEK (300) | 80 | 6 | 16.4 g | (82.6%) |
| 20 | —C$_6$H$_2$—Cl$_3$(2,4,5) | 15.0 | 7.1 | (0.070) | MEK (300) | 80 | 6 | 16.7 g | (84.2%) |
| 21 | —C$_6$H$_2$((OCH$_3$)$_2$(2,4), Cl(5)) | 15.4 | 5.9 | (0.058) | THF (200) | 65 | 6 | 17.8 g | (71.6%) |
| 22 | —C$_6$H$_3$(OCH$_3$(2), Cl(5)) | 13.9 | 6.0 | (0.060) | MEK (200) | 80 | 4 | 16.5 g | (92.0%) |
| 23 | α-naphthyl | 13.1 | 6.0 | (0.060) | MEK (250) | 80 | 3 | 13.7 g | (79.3%) |

In the above reaction, the amounts of reagents [II] and [III], solvents, temperature, reaction time and yield are shown in Table 2. The melting points and properties are shown in Table 1.

EXAMPLE 5

2-phenylcarbamoyl-3-methyl-5,6-dihydro-imidazo [2,1-b] thiazole (compound 1):

Compound 1 was prepared from compound 2 according to the following reaction schema:

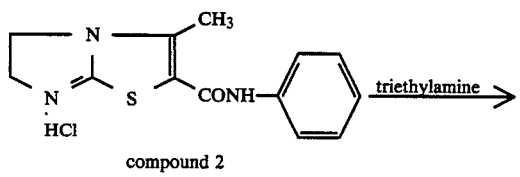

compound 2

Triethylamine was added to compound 2 (8.0 g, 0.027M) dissolved in water (200 ml), and the pH of the solution was adjusted to alkaline pH. The thus-formed precipitate was filtered, washed with water and dried to obtain compound 1. (70.0 g, yield: 100%).

m.p.: 204°–205° C., white powdery crystals.

EXAMPLE 6

2-(2-chlorophenylcarbamoyl)-3-methyl-5,6-dihydroimidazo [2,1-b] thiazole (compound 3):

2-(2-chlorophenylcarbamoyl)-3-methyl-5,6-dihydro-imidazo [2,1-b] thiazole hydrochloride (compound 4) (8.2 g, 0.025M) was dissolved in water (250 ml) and the insolubes were removed by filtration. To the solution was added 5% sodium hydroxide solution with stirring until an alkaline pH (pH 9–11) was reached. The precipitated crystals were filtered, washed and dried to obtain compound 3 as white powdery crystals. (7.2 g, yield: 98.2%).

m.p.: 212°–213° C.

EXAMPLE 7

2-(2,5-dichlorophenylcarbamoyl)-3-methyl-5,6-dihydroimidazo [2,1-b] thiazole (compound 7):

A small amount of active charcoal was added to 2-(2,5-dichlorophenyl-carbamoyl)-3-methyl-5,6-dihydro-imidazo [2,1-b] thiazole hydrochloride (compound 8) (9.1 g, 0.025M) dissolved in water (300 ml), and the mixture was stirred for 10 minutes and filtered. Pyridine was added to the filtrate with stirring to adjust the pH to alkaline. The precipitated crystals were collected by filtration, completely washed with water and dried to obtain compound 7 as white powdery crystals. (8.7 g, yield: 95.6%)

m.p.: 217°–219° C.

EXAMPLE 8

Compounds 5 and 24–38 were synthesized according to the method of Example 4. The amount of starting materials (compounds 6 and 9–23) (0.025M), the amount of water used, the base which was used for neutralization and the yield of the products (compounds 5 and 24–38) are shown in the following Table 3. The melting points and properties are shown in Table 1.

TABLE 3

| Starting material | | | | product | |
|---|---|---|---|---|---|
| compound No. | used g. | water used ml | base | compound No. | yield g. (%) |
| 6 | 8.2 | 250 | KOH | 5 | 6.9 (98.0) |
| 9 | 7.7 | " | Ba(OH)$_2$ | 24 | 6.8 (100) |
| 10 | 8.6 | " | Et$_3$N | 25 | 7.3 (94.8) |
| 11 | 8.1 | " | " | 26 | 7.0 (98.2) |
| 12 | 8.2 | " | α-picoline | 27 | 7.3 (99.1) |
| 13 | 8.6 | " | 4-dimethylaminopyridine | 28 | 7.2 (94.2) |
| 14 | 8.5 | " | γ-picoline | 29 | 7.1 (93.6) |
| 15 | 9.1 | 300 | NaOH | 30 | 8.0 (99.0) |
| 16 | 9.4 | 250 | " | 31 | 8.2 (97.3) |
| 17 | 9.1 | 300 | " | 32 | 7.8 (95.0) |
| 18 | 9.1 | " | N,N—dimethylaniline | 33 | 8.0 (97.1) |
| 19 | 10.0 | 350 | KOH | 34 | 9.0 (99.4) |
| 20 | 10.0 | " | " | 35 | 8.7 (96.7) |
| 21 | 9.7 | 250 | Na$_2$CO$_3$ | 36 | 8.2 (93.2) |
| 22 | 9.0 | " | " | 37 | 7.7 (95.3) |
| 23 | 8.6 | 300 | NaOH | 38 | 7.6 (98.7) |

EXAMPLE 9

Tablets (1000 Tab.):
Compound 15 25 g
J.P. D-mannitol 91 g
J.P. corn starch 53 g
J.P. CMC 200 mg
J.P. magnesium stearate 1 g The above mixture was placed in a V-shaped mixer and homogeneously mixed. The mixture was granulated to 20 mesh size by a dry-type roller. Tablets (1000 tablets, diameter 8.0 mm, thickness 2.6 mm, weight 170 mg) were prepared by a direct tabletting method using a plate-type tapping bar (diameter 8.0 mm).

EXAMPLE 10

Capsules (1000 Cap.):
Compound 15 25 g
J.P. D-mannitol 91 g
J.P. corn starch 63 g
J.P. CMC 200 mg
J.P. magnesium stearate 1 g The above mixture was placed in a V-shaped mixer and homogeneously mixed. The mixture was granulated by a dry-type roller, and encapsulated into hard capsules No. 4. Each capsule weighed 180 mg.

What is claimed is:

1. A compound of the formula

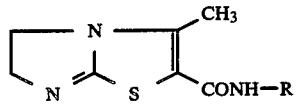

wherein R is chloro tolyl, dichlorophenyl, ethoxyphenyl, methoxychlorophenyl, trichlorophenyl or dimethoxychlorophenyl, or a pharmaceutically acceptable salt thereof.

2. A compound as claimed in claim 1, which is 2-(chlorotolylcarbamoyl)-3-methyl-5,6-dihydro-imidazo [2,1-b] thiazole or a pharmaceutically acceptable salt thereof.

3. A compound as claimed in claim 2, which is 2-(2-chloro-4-tolylcarbamoyl)-3-methyl-5,6-dihydro-imidazo [2,1-b] thiazole or a pharmaceutically acceptable salt thereof.

4. A compound as claimed in claim 2, which is 2-(4-chloro-2-tolylcarbamoyl)-3-methyl-5,6-dihydro-imidazo [2,1-b] thiazole or a pharmaceutically acceptable salt thereof.

5. A compound as claimed in claim 1, which is 2-(dichlorophenylcarbamoyl)-3-methyl-5,6-dihydro-imidazo [2,1-b] thiazole or a pharmaceutically acceptable salt thereof.

6. A compound as claimed in claim 5, which is 2-(2,4-dichlorophenylcarbamoyl)-3-methyl-5,6-dihydro-imidazo [2,1-b] thiazole or a pharmaceutically acceptable salt thereof.

7. A compound as claimed in claim 5, which is 2-(2,5-dichlorophenylcarbamoyl)-3-methyl-5,6-dihydro-imidazo [2,1-b] thiazole or a pharmaceutically acceptable salt thereof.

8. A compound as claimed in claim 1, which is 2-(ethoxyphenylcarbamoyl)-3-methyl-5,6-dihydro-imidazo [2,1-b] thiazole or a pharmaceutically acceptable salt thereof.

9. A compound as claimed in claim 8, which is 2-(4-ethoxyphenylcarbamoyl)-3-methyl-5,6-dihydro-imidazo [2,1-b] thiazole or a pharmaceutically acceptable salt thereof.

10. A compound as claimed in claim 1, which is 2-(methoxychlorophenylcarbamoyl)-3-methyl-5,6-dihydro-imidazo [2,1-b] thiazole or a pharmaceutically acceptable salt thereof.

11. A compound as claimed in claim 10, which is 2-(5-chloro-2-methoxyphenylcarbamoyl)-3-methyl-5,6-dihydro-imidazo [2,1-b] thiazole or a pharmaceutically acceptable salt thereof.

12. A compound as claimed in claim 1, which is 2-(trichlorophenylcarbamoyl)-3-methyl-5,6-dihydro-imidazo [2,1-b] thiazole or a pharmaceutically acceptable salt thereof.

13. A compound as claimed in claim 12, which is 2-(2,4,6-trichlorophenylcarbamoyl)-3-methyl-5,6-dihydro-imidazo [2,1-b] thiazole or a pharmaceutically acceptable salt thereof.

14. A compound as claimed in claim 1, which is 2-(dimethoxychlorophenylcarbamoyl)-3-methyl-5,6-dihydro-imidazo [2,1-b] thiazole or a pharmaceutically acceptable salt thereof.

15. A compound as claimed in claim 14, which is 2-(5-chloro-2,4-dimethoxyphenylcarbamoyl)-3-methyl-5,6-dihydro-imidazo [2,1-b] thiazole or a pharmaceutically acceptable salt thereof.

* * * * *